(12) United States Patent
Shoichet et al.

(10) Patent No.: US 7,541,381 B2
(45) Date of Patent: Jun. 2, 2009

(54) NON-COVALENT INHIBITORS OF AMPC β-LACTAMASE

(75) Inventors: Brian K. Shoichet, San Francisco, CA (US); Rachael A. Powers, Okemos, MI (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/368,790

(22) Filed: Feb. 19, 2003

(65) Prior Publication Data

US 2003/0232830 A1    Dec. 18, 2003

Related U.S. Application Data

(60) Provisional application No. 60/358,053, filed on Feb. 19, 2002.

(51) Int. Cl.
    *C07D 333/10*    (2006.01)
    *A61K 31/381*    (2006.01)
    *A61P 31/04*    (2006.01)

(52) U.S. Cl. ............. 514/438; 549/59; 549/62

(58) Field of Classification Search ........... 549/59, 549/62; 564/84, 85; 544/180, 182, 224, 544/238, 322, 336, 280, 290; 546/152, 297; 514/352, 306, 600, 602, 252.1, 256, 247, 514/241, 438; 515/352

See application file for complete search history.

(56) References Cited

U.S. PATENT DOCUMENTS

| | | | |
|---|---|---|---|
| 4,006,007 A | 2/1977 | Bollinger et al. | |
| 4,531,139 A | 7/1985 | Seitz | |
| 5,571,821 A | 11/1996 | Chan et al. | |
| 5,783,705 A | * 7/1998 | Blok et al. | ........ 548/247 |
| 5,939,431 A | 8/1999 | Solomon et al. | |

FOREIGN PATENT DOCUMENTS

| | | | |
|---|---|---|---|
| DE | 1155119 | * | 10/1963 |
| WO | WO-00/07997 A1 | * | 2/2000 |
| WO | WO02/22137 | | 3/2002 |

OTHER PUBLICATIONS

Clare et al. European Journal of Medicinal Chemistry, 34(6), 463-474, 1999.*
El-Maghraby et al. Egyptian journal of Pharmaceutical Sciences 24(1-4), 105-115, 1985.*
El-Maghraby et al. Proceeding of Indian National Science Academy, Part A, 53(3), 431-40, 1987.*
Babic et al., Drug Resistance Updates 9, 142-156, 2006.*
Paterson et al., Clinical Microbiological reviews 18(40, 657-686, 2005.*

* cited by examiner

*Primary Examiner*—Venkataraman Balasubramanian
(74) *Attorney, Agent, or Firm*—Reinhart Boener Van Deuren s.c.

(57) ABSTRACT

β-lactamases are the most widespread resistance mechanism to β-lactam antibiotics, such as penicillins and cephalosporins. In response to these enzymes, inhibitors have been introduced. Unfortunately, these inhibitors are also β-lactams, and resistance to them has developed rapidly. Consequently, the present invention provides a novel structure-based approach to inhibitors of these enzymes.

2 Claims, 5 Drawing Sheets

A.

B.

A.

B.

C.

though structurally distinguishable from the β-lactam antibiotics, and without the lactam ring structure, such compounds are non-covalent inhibitors of AmpC β-lactamase.

NON-COVALENT INHIBITORS OF AMPC β-LACTAMASE

This application claims priority benefit from provisional patent application Ser. No. 60/358,053 filed Feb. 19, 2002, the entirety of which is incorporated herein by reference.

The United States government has certain rights to this invention pursuant to Grant Nos. GM59957 and GM63815 from the National Institutes of Health to Northwestern University.

BACKGROUND OF THE INVENTION

β-lactams, such as penicillins and cephalosporins, are the most widely prescribed class of antibiotics. In response to their extensive use and misuse, bacterial resistance has developed. Continued usefulness is threatened by the expression of β-lactamase enzymes, the most widespread resistance mechanism to this class of antibiotics. These enzymes hydrolyze the lactam ring and render the antibiotic inactive against their original cellular targets, bacteria cell wall transpeptidases (FIG. 1).

In an effort to combat these enzymes, β-lactamase inhibitors, like clavulanic acid, and β-lactamase resistant compounds, like the third-generation cephalosporins, have been introduced (FIG. 2). Because these compounds are themselves β-lactams, bacteria responded rapidly to them; existing resistance mechanisms recognize the lactam ring functionality common to both substrates and inhibitors alike. These resistance mechanisms are easily disseminated among bacteria, allowing inhibitor resistance to spread rapidly. Novel inhibitors are required to avoid such pre-evolved resistance mechanisms.

It has been an on-going concern in the art to develop inhibitors that do not chemically and structurally resemble β-lactams, would not be hydrolyzed by β-lactamases, and would not be recognized by sensor proteins that bind β-lactams and upregulate the expression of β-lactamases. Additionally, a useful inhibitor would not be affected by porin channel mutants, which prevent access of β-lactams to their cellular targets. An inhibitor compound chemically and/or structurally dissimilar to a β-lactam minimizes the ability of bacteria to recruit and employ existing resistance mechanisms.

Several classes of non-β-lactam inhibitors of β-lactamases have been identified. Transition-state analog inhibitors, such as boronic acids and phosphonates, inhibit both class A and class C β-lactamases. Intensive study has been devoted to improving the binding affinities of these molecules. One concern with both types of molecules is the covalent adducts formed with activated serine nucleophiles, potentially reducing their specificity.

SUMMARY OF THE INVENTION

Figure 1:
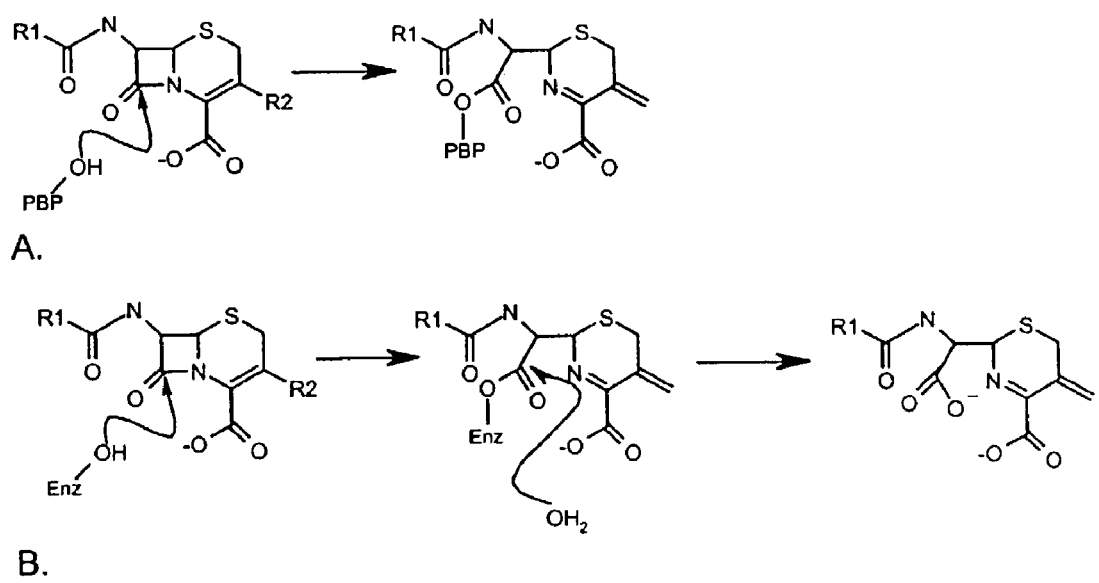
FIGS. 1A-B. Schematic illustrators of the mechanism of β-lactams and their inactivation by β-lactamases. 1A. β-lactams can form stable covalent complexes with their cellular targets, the transpeptidases. 1B. Serine β-lactamases can form transient covalent complexes with β-lactams that are rapidly hydrolyzed.

In light of the foregoing, it is an object of the present invention to provide a wide range of compounds, compositions and/or methods for their use in the inhibition of lactamase enzymes, thereby overcoming various deficiencies and shortcomings of the prior art, including those discussed above. It will be understood by those skilled in the art that one or more aspects of this invention can meet certain objectives, while one or more other aspects can meet certain other objectives, each objective may not apply equally, in all its respects, to every aspect of this invention. As such, the following objects can be viewed in the alternative with respect to any one aspect of this invention.

It is an object of the present invention to provide one or more compounds or compositions inhibiting lactamase activity, such compounds having neither chemical nor structural similarity to β-lactam antibiotics, in particular, such compounds absent the β-lactam ring structure of said antibiotics.

It can be another object of the present invention to provide one or more compounds, of the type consistent with the preceding objective, substantially without tendency to form covalent adducts adversely affecting their affinity for inhibitory lactamase interaction.

It can also be an object of the present invention to identify structural or functional moieties complimentary to or interactive with, in a non-covalent manner, with one or more lactam substrate recognition sites en route to compounds and/or compositions inhibiting lactamase activity.

Other objects, features, benefits and advantages of the present invention will be apparent from this summary and its descriptions of various preferred embodiments, and will be readily apparent to those skilled in the art having knowledge of enzyme activity and the inhibition thereof through strategic choice of structural relationships between such enzymes and substrate ligands complexed thereto. Such objects, features, benefits and advantages will be apparent from the above as taken into conjunction with the accompanying examples, data, figures and all reasonable inferences to be drawn therefrom.

The present invention relates, in part, to a structure-based approach to a class of novel, non-covalent inhibitors for AmpC β-lactamase (AmpC). As described more fully below, a consensus map of "hot spots" on AmpC was recently constructed, based on crystal structures of AmpC in complexes with thirteen different prior art ligands. The map was used to devise a molecular docking (DOCK) calculation to screen a database of over 200,000 small molecules for one or more structural features complementary to the binding site(s). Based on the results of this initial screen, fifty-six compounds were tested for inhibition of AmpC, and of these, three were shown to have apparent $K_i$ values of 650 μM or better (Table 1). Illustrating one or more aspects of this invention, compound 1, was further characterized kinetically and structurally. The structure of AmpC in complex with 1 was determined to 1.94 Å resolution by X-ray crystallography and compared to the DOCK prediction.

As mentioned above, all previously known inhibitors of AmpC β-lactamase form covalent adducts with the lactamase nucleophilic residue Ser64; with few exceptions, all are either β-lactams or molecules that mimic β-lactams. Conversely, compound 1 (see Table 1) forms a non-covalent complex, illustrating chemistry contrary to that exhibited by prior art inhibitors to bind to key substrate-recognition residues in the AmpC active site.

For the purposes of the present compounds, compositions and/or methods, the following expression(s) and word(s), unless otherwise indicated, will be understood as having the meanings ascribed thereto by those skilled in the art or as otherwise indicated with respect thereto:

"Cyclic alkene" means a structure containing one or more rings, each ring containing 4 to 8 carbon atoms, and at least one double bond. Without limitation, one or more carbon atoms may be oxidized to a corresponding carbonyl, and one or more rings may be aromatic. Representative cyclic alkenes include —$C_6H_5$ and

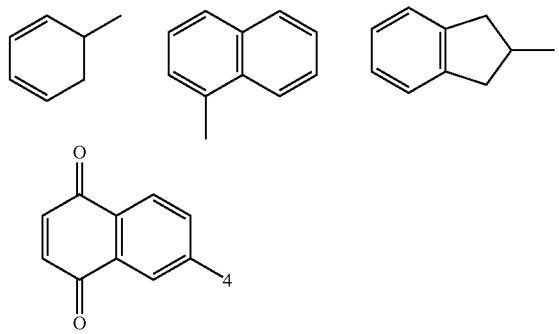

"Heterocyclic alkene" means a cyclic alkene as defined above wherein at least one carbon atom of at least one of the ring structures has been replaced by a heteroatom including but not limited to S, N or O. Representative heterocyclic alkenes include:

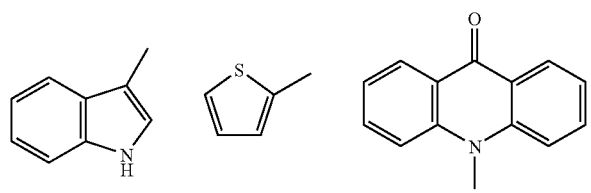

In part, the present invention comprises a method of inhibiting β-lactamase activity, the method comprising (1) providing a medium comprising AmpC-β-lactamase, and (2) introducing to and/or contacting the medium or the lactamase with a compound and/or composition comprising a compound which can be represented by the formula A-SO$_2$—NH—R, wherein A is an aryl, phenyl or thiophene moiety substituted with a carboxylate, a sulfonate or a tetraazolinyl group capable of binding with one or more lactamase substrate recognition residues electrophilic toward a β-lactam carbonyl functionality, and R is a cyclic alkene and/or heterocyclic alkene structural component/moiety capable of configurational interaction with lactamase substrate recognition residue Tyr221. Such a compound or composition is introduced to such a medium or contacted with a lactamase in an amount sufficient to inhibit lactamase activity.

Certain embodiments of the aforementioned compounds and/or compositions, as can be used in conjunction with the present methodologies, have a component A comprising phenyl, thiophene-2-yl and thiophene-3-yl moieties, any of which can be substituted with a carboxylate, sulfonate or tetraazolinyl group adjacent/ortho to the SO$_2$ moiety. With further reference to the aforementioned formula, R can be a cyclic alkene or a heterocyclic alkene, including but not limited to phenyl, biphenyl, pyridinyl, pyrazinyl, thiophenyl, pyrrolyl, fluorenyl, benzothiazyl, anthryl, naphthyl, 1,8-diazanaphthyl, 1,4,6,8-tetranaphthyl, 1-azanaphthyl, indenyl, purinyl, indolyl, pyrimidyl, pyridazyl, pyrazopyrimidyl, indazolyl, azaadenyl, adenosyl, 1,2,4-triazinyl, and 1,3,5-triazinyl. Such an R moiety can further comprise a substituent including but not limited to alkyl, cycloalkyl, arylalkyl, nitroalkyl, haloalkyl, alkoxyalkyl, hydroxyalkyl, aminoalkyl, azoalkyl, cyanoalkyl, amidoalkyl, alkoxycarbonylalkyl, carboxyalkyl, alkoxy, alkoxycarbonyl, hydroxy, amino, alkylamino, cycloalkylamino, arylamino, amidocarbonyl, alkylcarboxamido, arylcarboxamido, carboxy, formyl, alkylcarbonyl, arylcarbonyl, carboxycarbonyl, sulfonyl, alkylsulfonyl, sulfoxy, sulfamoyl, nitrile, azo, alkylazo, arylazo, hydrazinyl, hydrazincarbonyl, nitroso, nitro, cyclicalkenyl, heterocyclicalkenyl and combinations thereof.

Numerous other compounds, as can be used in conjunction with the compositions and methods of this invention, can comprise structural or compositional variations of A or R, or a substituent thereof, having, respectively, binding, complexing and/or interactive capabilities in accordance with this invention, with one or more β-lactamase substrate recognition residues electrophilic with respect to a β-lactam substrate and/or configurational or spatial interactive capabilities with a lactamase substrate recognition residue Tyr221.

More specifically, moiety A can vary by way of structure or substituent, limited only by the effect of such variation(s) on the binding or interaction of the sulfonamide group with a β-lactamase, the pertinent lactam substrate amide recognition residues thereof and/or inhibition of the lactamase enzyme. The aforementioned carboxylate, sulfonate or tetraazolinyl groups can, in the alternative, be replaced by one or more substituents and/or functional groups, limited only by the effect of such variation on binding or interaction with the "oxyanion" or "electrophilic" hole of a β-lactamase, the pertinent lactam substrate recognition residues thereof and/or inhibition of the lactamase enzyme. Likewise, moiety R can vary by way of structure or substituent, limited only by the effect of such variation(s) on the binding or interaction with a β-lactamase, the conserved Tyr221 residue or a functionally-equivalent residue thereof and/or inhibition of the lactamase enzyme. Such variations are in accordance herewith, would be understood by those skilled in the art made aware of this invention, and are consistent with the structural relationships described herein.

With respect to either the compounds, compositions and/or methods of the present invention, the A and R moieties or components can comprise, consist of, or consist essentially of any of the aforementioned substituents and functional groups thereof. Each such compound or moiety/substituent thereof is distinguishable, characteristically contrasted, and can be practiced in conjunction with the present invention separate and apart from another. Accordingly, it should also be understood that the inventive compounds, compositions and/or methods, as illustratively disclosed herein, can be practiced or utilized in the absence of any one compound, moiety and/or substituent which may or may not be disclosed, referenced or inferred herein, the absence of which may or may not be specifically disclosed, referenced, or inferred herein.

Representative compounds and compositions, in accordance with this invention and illustrating one or more aspects thereof, are provided in a number of tables included herewith. In particular, reference is made to Table 6 (compounds 10 and 1) showing a number of such thiophene and aryl compounds, the preparation of which are as schematically shown therein, or as would otherwise be known to those skilled in the art made aware of this invention, using straight-forward synthetic techniques or modifications thereof, depending upon the particular thiophene or aryl precursor components (A and/or C substituent) or the identity of the R and its corresponding precursor component.

More particularly, the present invention can also comprise a method of using a sulfonamide functional moiety to inhibit β-lactamase activity. The method includes (1) providing a compound having a sulfonamide functional moiety capable of binding to a lactamase site recognizing the amide side chain of a β-lactam substrate; and (2) adding or introducing the sulfonamide compound or a composition thereof to a medium including AmpC-β-lactamase, such a compound/composition in an amount or having a concentration sufficient to inhibit lactamase activity. In certain embodiments, such a sulfonamide functionality is a substituent to a phenyl or a thiophenyl moiety. In preferred embodiments, the compound further includes a second substituent group/moiety capable of binding to a lactamase site electrophilic toward a β-lactam carbonyl functionality. Such a second substituent moiety can include but is not limited to a carboxylate, sulfonate or a tetraazolinyl group. Regardless, certain other embodiments can include a third moiety bonded to the nitrogen center of the sulfonamide moiety and capable of configurational or spatial interaction with a lactamase substrate recognition residue Tyr221.

In part, the present invention can also include a composition comprising an AmpC-β-lactamase component and a ligand component, in accordance with this invention, non-covalently associated, bonded and/or complexed therewith. The ligand component has a sulfonamide moiety capable of binding to a lactamase site recognizing the amide side chain of a β-lactam substrate, and further includes a second moiety capable of binding to a lactamase site responsible for electrophilic interaction with the carbonyl group of a β-lactam substrate. As associated or complexed therewith, such ligand is capable of inhibiting lactam hydrolysis by the lactamase component. In certain and/or preferred embodiments of this method, the second moiety is a carboxylate functional group. Other such second moieties can include sulfonate and tetraazolinyl functional groups. Such a ligand component can comprise a compound of the preceding formula and/or any metabolic or decomposition analog thereof or intermediate en route thereto.

The compounds of this invention may contain an acidic or basic functional group and are, thus, capable of forming pharmaceutically-acceptable salts with pharmaceutically-acceptable acids and bases. The term "pharmaceutically-acceptable salts" refers to the relatively non-toxic, inorganic and organic acid and base addition salts of such compounds. These salts can be prepared by reacting the purified compound with a suitable acid or base. Suitable bases include the hydroxide, carbonate or bicarbonate of a pharmaceutically-acceptable metal cation, ammonia, or a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

As mentioned above, the compounds of this invention, and the pharmaceutically-acceptable salts thereof, are inhibitors of β-lactamases. Assays for the inhibition of β-lactamase activity are well known in the art. For instance, the ability of a compound to inhibit β-lactamase activity in a standard enzyme inhibition assay may be used (see, e.g., Example 1 below and M. G. Page, *Biochem J.* 295 (Pt. 1) 295-304 (1993)). β-lactamases for use in such assays may be purified from bacterial sources or, preferably, are produced by recombinant DNA techniques, since genes and cDNA clones coding for many β-lactamases are known. See, e.g., S. J. Cartwright and S. G. Waley, *Biochem J.* 221, 505-512 (1984). Alternatively, the sensitivity of bacteria known, or engineered, to produce a β-lactamase to an inhibitor may be determined. Other bacterial inhibition assays include agar disk diffusion and agar dilution. See, e.g., W. H. Traub & B. Leonhard, *Chemotherapy* 43, 159-167 (1997). Thus, a β-lactamase can be inhibited by contacting the β-lactamase enzyme with an effective amount of an inventive compound or by contacting bacteria that produce the β-lactamase enzymes with an effective amount of such a compound so that the β-lactamase in the bacteria is contacted with the inhibitor. The contacting may take place in vitro or in vivo. "Contacting" means that the β-lactamase and the inhibitor are brought together so that the inhibitor can bind to the β-lactamase. Amounts of a compound effective to inhibit a β-lactamase may be determined empirically, and making such determinations is within the skill in the art. Inhibition includes both reduction and elimination of β-lactamase activity.

The present compounds, and the pharmaceutically-acceptable salts thereof, can be used to treat β-lactam-antibiotic-resistant bacterial infections. "β-lactam-antibiotic-resistant bacterial infection" is used herein to refer to an infection caused by bacteria resistant to treatment with one or more β-lactam antibiotics due primarily to the action of a β-lactamase. Resistance to β-lactam antibiotics can be determined by standard antibiotic sensitivity testing. The presence of β-lactamase activity can be determined as is well known in the art (see above). Alternatively, the sensitivity of a particular bacterium to the combination of an inventive compound, or a pharmaceutically-acceptable salt thereof, and a β-lactam antibiotic can be determined by standard antibiotic sensitivity testing methods.

To treat a β-lactam resistant bacterial infection, an animal or subject suffering from such an infection is given an effective amount of a compound of this invention, or a pharmaceutically-acceptable salt thereof, and an effective amount of a β-lactam antibiotic. Such a compound, or a pharmaceutically-acceptable salt thereof, and the β-lactam antibiotic may be given at different times or given together. When administered together, they may be contained in separate pharmaceutical compositions or they may be in the same pharmaceutical composition.

Many suitable β-lactam antibiotics are known in the art, including but not limited to the cephalosporins, penicillins, monobactams, carbapenems, and carbacephems. β-lactam antibiotics are effective (in the absence of resistance) against a wide range of bacterial infections. These include those caused by both gram-positive and gram-negative bacteria, for example, bacteria of the genus Staphylococcus (such as *Staphylococcus aureus* and *Staphylococcus epidermidis*), Streptococcus (such as *Streptococcus agalactine, Streptococcus penumoniae* and *Streptococcus faecalis*), Micrococcus (such as *Micrococcus luteus*), Bacillus (such as *Bacillus subtilis*), Listerella (such as *Listerella monocytogenes*), Escherichia (such as *Escherichia coli*), Klebsiella (such as *Klebsiella pneumoniae*), Proteus (such as *Proteus mirabilis* and *Proteus vulgaris*), Salmonella (such as *Salmonella typhosa*), Shigella (such as *Shigella sonnei*), Enterobacter (such as *Enterobacter aerogenes* and *Enterobacter cloacae*), Serratia (such as *Serratia marcescens*), Pseudomonas (such as *Pseudomonas aeruginosa*), Acinetobacter such as *Acinetobacter anitratus*), Nocardia (such as *Nocardia autotrophica*), and Mycobacterium (such as *Mycobacterium fortuitum*). Effective doses and modes of administration of β-lactam antibiotics are known in the art or may be determined empirically or as described below for such compounds.

To treat an animal/subject suffering from a β-lactam-antibiotic-resistant bacterial infection, an effective amount of one or more of the present compounds, or a pharmaceutically-acceptable salt thereof, is administered in combination with a β-lactam antibiotic. Effective dosage forms, modes of administration and dosage amounts may be determined empirically, and making such determinations is within the skill of the art. It is understood by those skilled in the art that the dosage amount will vary with the activity of the particular compound employed, the severity of the bacterial infection, the route of administration, the rate of excretion of the compound, the duration of the treatment, the identity of any other drugs being administered to the animal/subject, the age, size and species of the animal, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of such a compound, or a pharmaceutically-acceptable salt thereof, maybe administered as two, three, four, five, six or more sub-doses, administered separately at appropriate intervals throughout the day. Treatment of a β-lactam-antibiotic-resistant bacterial infection according to the invention, includes mitigation, as well as elimination, of the infection. Animals treatable according to the invention include mammals. Mammals treatable according to the invention include dogs, cats, other domestic animals, and humans.

Compounds of this invention may be administered to an animal/patient for therapy by any suitable route of administration, including orally, nasally, rectally, intravaginally, parenterally, intracisternally and topically, as by powders, ointments or drops, including buccally and sublingually. The preferred routes of administration are orally and parenterally.

While it is possible for the active ingredient(s) (one or more compounds of this invention and/or pharmaceutically-acceptable salts thereof, alone or in combination with a β-lactam antibiotic) to be administered alone, it is preferable to administer the active ingredient(s) as a pharmaceutical formulation (composition). The pharmaceutical compositions of the invention comprise the active ingredient(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat, (3) topical application, for example, as a cream, ointment or spray applied to the skin; or (4) intravaginally, for example, as a pessary, cream or foam.

DETAILED DESCRIPTION OF CERTAIN EMBODIMENTS

Figure 2:
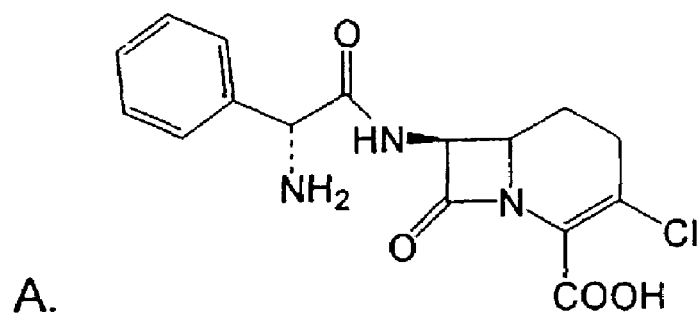
FIGS. 2A-C. Comparison of the chemical structures of several β-lactamase ligands. 2A. Loracarbef, a β-lactamase substrate of the prior art. 2B. Ceftazidime, a β-lactamase resistant molecule of the prior art. 2C. Compound 1 of this invention, 3-[(4-chloroanilino) sulfonyl]thiophene-2-carboxylic acid, a lactamase inhibitor, in accordance with this invention.
Figure 2:
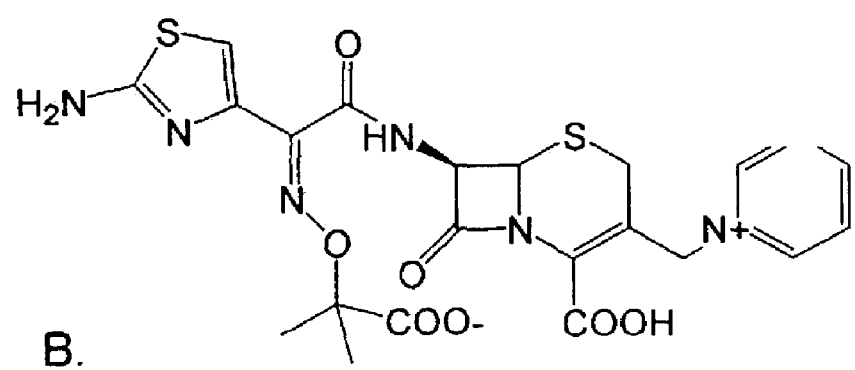
Figure 2:
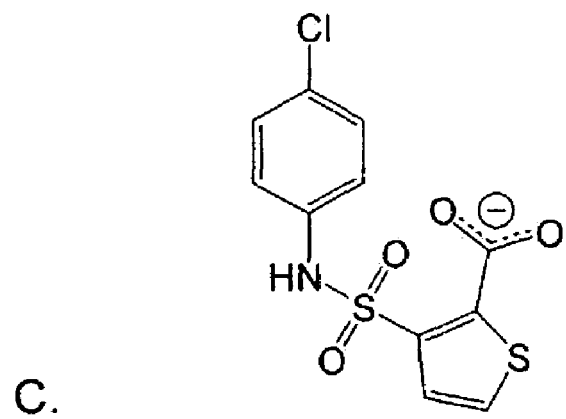

Several aspects or features of the present invention can be illustrated with reference to compounds 1-3. Without restriction to any one theory or mode of operation, the sulfonamide group of compound 1 is believed to bind in the enzyme site that recognizes the ubiquitous C6(7)-amide side chains of β-lactams, where it hydrogen-bonds with two of the amide recognizing enzyme residues, Asn152 and Ala318. Although these hydrogen bonds resemble those made by made by the amide side chains of β-lactams, the atom order of the sulfonamide side chain in 1 is the reverse of that in the amide side chain of β-lactams (FIG. 2). Additionally, one of the oxygen atoms of the carboxylate group of 1 is believed to bind in the "oxyanion" or "electrophilic" hole of the β-lactamase, hydrogen bonding to the main chain nitrogens of residues Ser64 and Ala318. This resembles the interactions made by the carbonyl oxygen atom of β-lactams with these residues in several acyl-enzyme complexes of β-lactamases with β-lactams. As can relate to another feature of this invention, the terminal chlorophenyl ring of the 1 stacks with the conserved Tyr221, similar to the aryl rings found in β-lactams such as cephalothin, loracarbef, and ceftazidime.

Numerous interactions believed useful in this invention were captured in the docking calculation that led to the discovery of this class of inhibitor compositions. The RMSD between the docked and experimental structures varied from 1.7-1.9 Å, depending on which molecule in the asymmetric unit was used in the comparison. Notwithstanding this quantitative difference, qualitatively and visually the two structures resemble each other closely. Of the ten hydrogen bonds observed in the X-ray structure, seven were predicted in the docked complex, and both of the two major non-polar interactions were predicted. The major difference between the docked and X-ray configurations is a consequence of the rotation of the chlorophenyl ring by 90° that results in a herring-bone rather than a π-stacking interaction between this ring and Tyr221.

Consistent with experimental observations, the docking energy scores suggest that the carboxylate and sulfonamide functionalities of compound 1 are useful binding determinants. To investigate this further, analogs of 1 were tested as inhibitors. Replacing the carboxylate with a methyl ester (5) or a nitro group (9) compromised inhibition, consistent with the prediction. (See, Table 5.) Switching the order of the sulfonamide (cpd 4, Table 5) diminished inhibition threefold, suggesting that this unusual amide arrangement is nevertheless useful in this non-covalent inhibitor. In light of the present invention, these effects seem sensible, since in the crystal structure this carboxylate hydrogen bonds with the enzyme; any disruption of these interactions would be expected to adversely affect affinity.

Previously determined structures of AmpC complexes were used to flag hot spots for binding and to identify tightly bound water molecules. Based on thirteen previously determined structures of the prior art, consensus binding sites were identified for an amide/aryl site, a carbonyl/hydroxyl site, a hydroxyl site, a carboxylate site, and a hydrophobic site. In their docked complexes, new inhibitor compounds 1-3 of this invention exploited these hot spots; for example, an oxygen atom, from the carboxylate group of 1 and 3 and the sulfate group of 2, was predicted to bind in the carbonyl/hydroxyl site, and the hydrophobic site was complemented with hydrophobic portions of each of these compounds. Intriguingly, however, new inhibitor compounds 1-3 took advantage of the consensus hot spots using functionality not found in the thirteen prior art ligands used to identify the hot spots in the first place. Therefore, the prior art did not suggest placement of a sulfonamide group in the amide recognition site of AmpC; did not position a carboxylate or related group into the "oxyanion" hole of the β-lactamase; and did not suggest the benzoaminothiazole ring found in compounds 2 and 3.

The inclusion of bound water molecules in the setup of the docking experiment also came out of analysis of the thirteen previous complexes used to identify the consensus hot spots. Water molecules included as part of the receptor can influence what ligands are identified in a docking calculation, both by acting as a point of interaction for the docked molecules and by excluding them from occupying the volume that the water itself occupies. Consequently, there is much interest in how water influences the results of docking and structure-based design calculations. Based on analysis of waters found conserved in AmpC structures, three waters were treated as non-displaceable parts of the receptor: Wat403, Wat404, and Wat405. Wat404 and Wat405 are relatively distant from the site of docking and will not be considered further. Wat403 is at the center of the active site. Water was used in the docking calculation because it is highly conserved in all AmpC structures (present in 29 of 30 molecules previously examined) and because it is well coordinated by the enzyme. The inclusion of water appears to have influenced that calculation beneficially, as it hydrogen bonds with the inhibitor in both the docked and the crystallographic structures of compound 1 bound to AmpC. Accordingly, various aspects of this invention contemplate, in a broader context, an lactamase/inhibitor complex or association in the presence of any such water molecules.

As described more fully below, representing the broader utility of this invention, compound 1 exhibits selectivity for AmpC β-lactamase over several mechanistically related serine proteases. It binds at least two hundred-fold better to AmpC than to trypsin or elastase, and it is selective by at least sixty-fold more selective for AmpC over chymotrypsin. Compound 1 reversed β-lactam resistance in a strain of bacteria that overexpresses β-lactamase. Compound 1 to potentiated the activity of the β-lactam ampicillin against a strain of resistant bacteria, increasing the efficacy of ampicillin by four-fold and reducing its minimum inhibitory concentration (MIC) to 128 μg/ml.

Illustrating one or more aspects of this invention, compound 1 is a competitive, non-covalent inhibitor of AmpC with a $K_i$ value of 23 μM. Compared to more traditional covalent inhibitors of AmpC, this is a modest level of inhibition. Nevertheless, the compound holds promise as a lead for drug discovery: it explores novel chemical functionality, which it uses to complement key recognition residues of the β-lactamase. The recognition "code" of the AmpC structure appears to be plastic, not only are β-lactams recognized by highly conserved active site residues, but compounds bearing very different functionality can also bind. Notwithstanding its modest level of inhibition, compound 1 reversed antibiotic resistance in bacterial cell culture and would be expected to do so, in vivo. The compound was specific to AmpC and did not inhibit related serine amidases in counter-screens. Finally, it is relatively "drug-like", passing four of four Lipinski rules and having several places for synthetic elaboration whereby analogs might be explored. The ability to discover such inhibitors through structure-based techniques, and the correspondence between the docking prediction and the experimental result, holds promise for the development of this and other families of novel inhibitors of serine β-lactamases. Such novel inhibitors are much needed as β-lactamase-mediated antibiotic resistance continues to spread among bacterial pathogens.

EXAMPLES OF THE INVENTION

The following non-limiting examples and data illustrate various aspects and features relating to the compounds, compositions, complexes and/or methods of the present invention, including the use of the compositions described herein to inhibit lactamase activity, such compounds and/or compositions as are available through these synthetic methodologies described herein. In comparison with the prior art, the present compositions and/or methods provide results and data which are surprising, unexpected and contrary thereto. While the utility of this invention is illustrated through the use of several compounds/compositions and structural moieties presented therewith, it will understood by those skilled in the art that comparable results are obtainable with various other compounds/compositions, as are commensurate with the scope of this invention.

Example 1

Northwestern University DOCK was used to screen the Available Chemicals Directory (ACD), a database of 229,810 commercially available small molecules. The docking experiment incorporated information about hot spots identified on AmpC using a consensus overlay. This consensus map, based on crystal structures of AmpC in complexes of nine boronic acid inhibitors and four β-lactam ligands, identified several favorable binding sites on AmpC: an amide recognition site, a hydrophobic site, an aryl site, a carboxylate site, a carbonyl/hydroxyl site, and a hydroxyl site, along with several conserved water sites. Each of these binding sites was included in the docking experiment as part of the sphere set used to orient the rigid fragment of the ligands in the target site, and chemical matching was used to indicate the type of functionality recognized at the site. Two docking calculations, differing in the partial atomic charges of several active site residues, were performed. The magnitudes of local partial atomic charges were increased, without changing the overall charges of a residue, in an effort to capture the polarization thought to occur when hydrogen bonding to these residues. This was done to improve polar complementarity between AmpC and the ligands in the docking calculation.

Figure 3A:
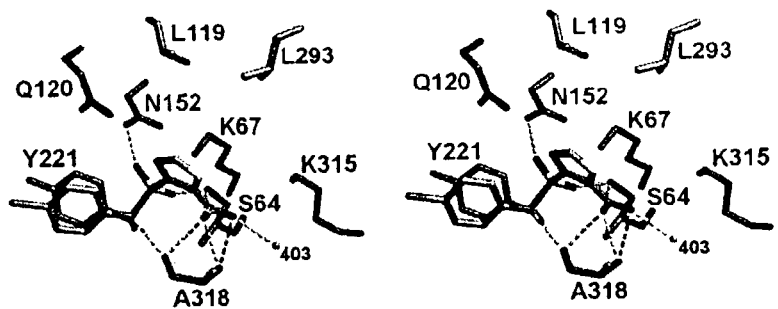
FIGS. 3A-C. Stereo view of the interactions observed between AmpC and compounds 1-3 in the DOCK predicted orientations. 3A. Compound 1. 3B. Compound 2. 3C. Compound 3. Hydrogen bonds are shown as dashed lines. Spheres represent water molecules. All figures were generated with MidasPlus, unless otherwise noted.
Figure 3B:
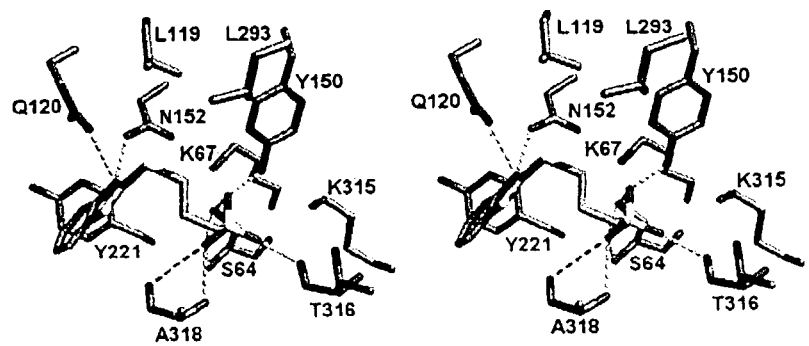
Figure 3C:
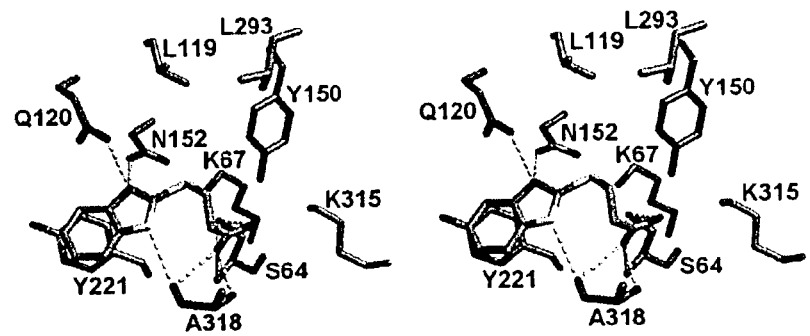
Figure 4A:
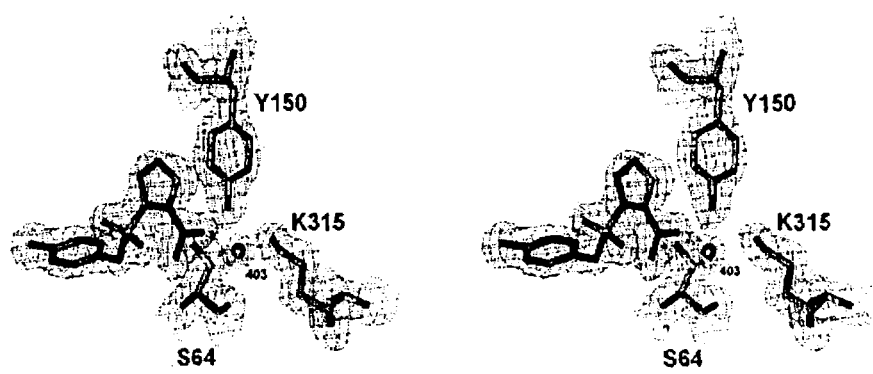
FIGS. 4A-B. Stereo view of the active site region of the AmpC/1 complex determined to 1.94 Å resolution. 4A. The $2F_o-F_c$ electron density map is shown, contoured at $1.0\sigma$. This figure was made with SETOR. 4B. Interactions observed between AmpC and 1 in the crystallographic complex. Spheres represent water molecules. Dashed lines indicate hydrogen bonds.
Figure 4B:
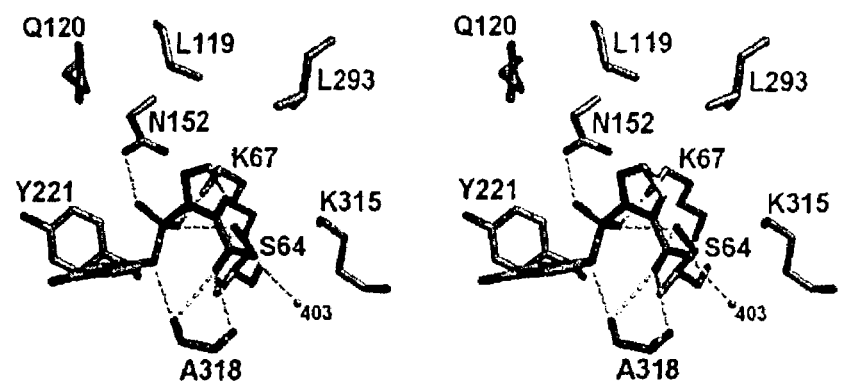

The top five hundred molecules from each docking run were examined graphically for complementarity to the enzyme, for polar interactions with active site residues, and for agreement with binding sites identified in the consensus map. From the two lists, fifty-six compounds were tested for inhibition of AmpC. Three molecules inhibited AmpC with $K_i$ values of 800 μM or better (compounds 1-3; Table 1). Compound 1 ranked 115$^{th}$ out of 500, 2 ranked 384$^{th}$, and 3 ranked 415$^{th}$ in the list where the dipole was increased the most; these compounds were not present in the other top five hundred list. The DOCK-predicted conformations of these compounds and their interactions with AmpC are shown in FIG. 3. The best inhibitor, compound 1, is a competitive, reversible inhibitor of AmpC with a $K_i$ value of 23 μM for AmpC. This compound was also tested for activity against the mechanistically related serine proteases α-chymotrypsin, β-trypsin, and elastase (Table 1). Compound 1 showed no inhibition of trypsin and elastase at concentrations up to 4 mM and was greater than fifty-fold more selective for AmpC over chymotrypsin.

Example 2

Several intriguing interactions are observed between AmpC and 1 in the DOCK-predicted orientation (FIG. 1B; Table 2). The carboxylate group is placed near the catalytic Ser64. One of the oxygens of the carboxylate interacts with Oγ of Ser64 and with the main chain nitrogen and oxygen atoms of Ala318; the other oxygen interacts with the main chain nitrogen of Ala318 and Wat403, a conserved water molecule that was included in the docking experiment as part of the receptor. The thiophene ring is placed in the hydrophobic binding site formed by Leu119 and Leu293; distances to these residues are approximately 5.1 Å. One of the sulfonamide oxygens interacts with Oγ of Ser64, and the other oxygen interacts with Nδ2 of Asn152. The nitrogen of the sulfonamide interacts with the main chain oxygen of Ala318. Finally, the chlorophenyl ring appears to π-π stack with Tyr221. Several of these interactions agree with the consensus map; the Leu119/ Leu293 hydrophobic patch is complemented with the thiophene ring, and one of the carboxylate oxygens is placed in the "oxyanion" or "electrophilic" hole, which can bind carbonyl and hydroxyl groups.

Example 3

Subsequently, the structure of AmpC in complex with compound 1 was determined by X-ray crystallography to 1.94 Å resolution (FIG. 6; Table 3). The location of the inhibitor in each of the two active sites was unambiguously identified in the initial $F_o$-$F_c$ difference maps when contoured at a level of 3σ. In addition, $F_o$-$F_c$ difference electron density indicated the presence of a third inhibitor molecule located at the interface between the two molecules. A simulated annealing omit map of the refined model agreed well with the conformation of the inhibitor in each site (not shown). The quality of the final model of the complex was analyzed with the program Procheck; 92.5% of the non-proline, non-glycine residues are in the most favored region of the Ramachandran plot (7.5% in the additionally allowed region).

Example 4

Figure 5:
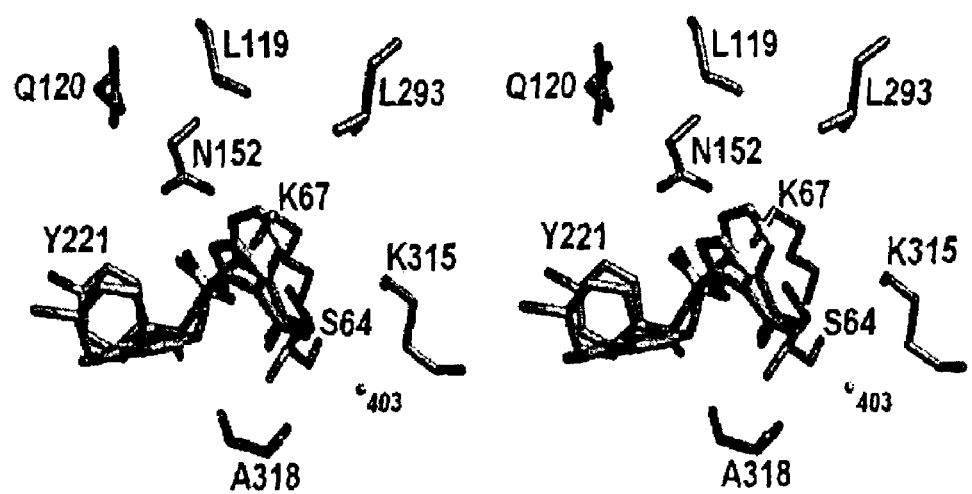
FIG. 5. Overlay of the docked and crystallographic conformations of 1 in the AmpC site.

In the experimentally determined structure, 1 interacts with several active site residues (FIG. 5; Table 3). The carboxylate group is bound near Ser64, with one of its oxygens interacting with the main chain nitrogen and Oγ atoms of Ser64 and the main chain nitrogen and oxygen of Ala318. The other oxygen of the carboxylate hydrogen bonds with Wat403 and in molecule 2, with Wat481. The thiophene ring is within van der Waals distance to residues Leu119 and Leu293 (distances range from 4.2 to 4.6 Å) that form a hydrophobic patch on AmpC. One of the sulfonamide oxygen atoms hydrogen bonds with Oγ of Ser64 and Nζ of Lys67; the other interacts with Nδ2 of Asn12. The nitrogen atom of the sulfonamide group interacts with the main chain oxygen of Ala318. The chlorophenyl ring appears to be involved with quadrupole-quadrupole interactions with Tyr221; the distance between the centroids of these two rings is between 5.5 and 5.8 Å, and the angle of interaction ranges from 91 to 94°.

Example 5

The DOCK-predicted conformation of I closely resembles the experimentally determined structure (FIG. 5); the RMSD for all inhibitor atoms is 1.867 Å, when matching molecule 2 of both structures (RMSD Cα 0.14 Å), and 1.750 Å, when matching molecule 1 of the crystal structure to molecule 2 of the DOCK structure (RMSD Cα 0.26 Å). In the crystal structure, the entire molecule is shifted and slightly rotated from the predicted conformation. Despite this shift, most of the interactions between AmpC and 1 in the predicted conformation are also observed in the experimental structure. Of the nine hydrogen bonding interactions observed in both monomers in the crystallographic complex, seven are also observed in the docked prediction (Table 3). For instance, the key interactions between the sulfonamide oxygen O17 and Asn152Nδ2 and the sulfonamide nitrogen N1 and Ala318O are observed in both the experimental structure and the prediction. Interactions between the sulfonamide oxygen O16 and Lys67Nδ and the carboxylate oxygen and Ser64N are only observed in the crystal structure. The largest difference between the two structures is the orientation of the chlorophenyl ring; in the crystal structure, this ring has rotated approximately 60°, as measured by the dihedral angle around S13, N1, C2, C3. This ring now interacts in a more edge-to-face manner with Tyr221, presumably making quadrupole-quadrupole interactions with Tyr221 instead of the π-π stacking observed in the predicted structure.

The ability of compound 1 was investigated to potentiate the activity of a β-lactam against a strain of resistant bacteria. In bacterial cell culture, compound 1 increased the efficacy of ampicillin by four-fold and reduced its minimum inhibitory concentration (MIC) to 128 μg/ml (Table 4). At this concentration compound 1 alone had no measurable antibiotic activity.

The structure of the AmpC/1 complex allowed use of a structure-guided approach to search for analogs of compound 1. In an effort to determine the structure-activity relationship of this series and identify compounds with improved binding affinity, six commercially available analogs from the ACD were ordered and tested (compounds 4-9; Table 5). The carboxylate group appears to be a preferred structure or functionality; binding was somewhat problematic with the ester (5) and nitro (9) analogs. Switching the atom order of the sulfonamide group (4) reduced binding by three-fold. Disruption of the proton donating ability of the sulfonamide nitrogen (6) through incorporation into a piperazine ring system also hindered binding. With compound 7, the addition of a piperidine ring ortho to the sulfonamide group showed a slight improvement in affinity ($K_i$ 14 μM). Referring to Table 6 and consistent with the structure-activity relationships of this invention, the range of compounds 9-10 can also be utilized, in accordance herewith.

Example 6

Docking. The Available Chemicals Directory was screened against molecule 2 of native AmpC (PDB entry 1KE4) using the Northwestern University version of DOCK. To prepare the site for docking, all water and ion molecules were removed, except for Wat403, Wat404, and Wat405. These specific water molecules were included as part of the receptor because they are observed in nearly all AmpC structures and are believed to be integral in maintaining protein structure. Protonation of receptor residues and water molecules was done with Sybyl (Tripos, St. Louis, Mo.). Positions of some protons were then changed manually to more appropriate orientations in MidasPlus. The sphere set used was based on ligand atom positions from an ensemble of structures of nine boronic acid inhibitors and four β-lactam molecules determined in complex with AmpC β-lactamase by X-ray crystallography. This resulted in one cluster of 73 spheres, each of which represented a ligand atom position observed in the X-ray structures, which was used in the docking calculation. The spheres were labeled based on the chemical functionality of the ligand atoms they represented. Force field and electrostatic grids were calculated with CHEMGRID and DelPhi, respectively. DISTMAP was used to calculate the excluded volume grid.

Example 7

In the docking calculation, calculated interaction energies were corrected for ligand desolvation using AMSOL, which was also used to calculate ligand partial atomic charges. Each orientation of the docked ligands was refined with one hundred iterations of rigid-body minimization. The distance tolerance parameter for calculating orientations was set to 1.2 Å. The ligand and receptor bin sizes were each 0.2, and ligand and receptor overlap were also each 0.2. Chemical matching was used to specify how ligand atoms were to be matched to the spheres. To improve hydrogen bonding opportunities between active site residues and the ligands, the absolute magnitude of the partial atomic charges of the following active site residues were increased by 0.4 units and in a second docking calculation, by 0.8 units: Ser64Oγ and Hoγ; Gln120Oε1, HNε1, and HNε2; Tyr150OH and HOH; Asn152Oδ1, HNδ1, and HNδ2; Tyr221OH and HOH; Asn289Oδ1, HNδ1, and HNδ2; Thr316Oγ1 and Hoγ; Ala318O and HN; Asn343Oδ1, HNδ1, and HNδ2; and Asn346Oδ1, HNδ1, and HNδ2; for the asparagines and glutamine residues, the charge increase was split among the protons on the amide groups. The top scoring five hundred molecules from each docking run were displayed with MidasPlus. From these two lists, a total of fifty-six compounds were ordered and tested for inhibition of AmpC.

Example 8

Enzymology. AmpC from *Escherichia coli* was expressed and purified to homogeneity as described in the literature. Compound 1, 3-[(4-chloroanilino)sulfonyl]thiophene-2-carboxylic acid, 4, 2-methyl-4-[[(4-methylphenyl)sulfonyl] amino]thiophene-3-carboxylic acid, 5, methyl 3-[(4-chloroanilino)sulfonyl]thiophene-2-carboxylate, 6, 3-([4-[3-chloro-5-(trifluoromethyl)pyridin-2-yl]piperazino]sulfonyl) thiophene-2-carboxylate, 7, 3-[(2-piperidinoanilino)

sulfonyl]thiophene-2-carboxylic acid, and 8, 2,5-dimethyl-4-(2-thienylaminosulfonyl)furan-3-carboxylic acid, were obtained from Maybridge Chemical, (Cornwall, UK). Compound 2, 3-(2-benzothiazolylthio)-1-propanesulfonic acid, and 9, N-(4-methoxyphenyl)-2-nitro-benzenesulfonamide, were obtained from Aldrich Chemical (Milwaukee, Wis.). Compound 3, 3-(2-benzothiazolylthio)propionic acid, was obtained from TCI America (Portland, Oreg.). All were used without further purification. Kinetic measurements with AmpC were performed in 50 mM TRIS buffer, pH 7.0, using nitrocefin as a substrate. The Km of nitrocefin for AmpC in this buffer was determined to be 127 µM. Reactions were initiated by the addition of 0.875 nM enzyme and monitored in methacrylate cuvettes. No incubation effect was detected for any compound. $IC_{50}$ values were determined at 200 µM substrate concentration. $K_i$ values for the compounds were obtained by comparison of progress curves in the presence and absence of inhibitor. Sufficient inhibitor was used to give at least 50% inhibition. This method correlates well with full $K_i$ analysis through coupled substrate and inhibitor concentration variation. For compound 1, a $K_i$ consistent with the value of 23 µM determined by progress curve analysis, was also determined by Lineweaver-Burk analysis of multiple substrate and inhibitor concentrations. Comparable enzymatic techniques and analyses can be used to demonstrate the utilities corresponding to other compounds or compositions of this invention.

The compounds of this invention are typically synthesized from available starting materials and reagents, via corresponding condensation reactions and related procedural techniques. Other methodologies are of the sort used to prepare several of those compounds comercially-available, and useful with the compositions and methods of this invention. For instance and without limitation, precursors B in Table 6, all known and available starting materials or synthetically-available, can be utilized to provide inventive compounds 9 or 10 with a particular R moiety, through condensation with a particular precursor to a desired A moiety (again, known and comercially available or prepared via the literature)—using known synthetic techniques or straight-forward modifications thereof, each as would be well-known to those skilled in the art of synthetic organic chemistry and without undue experimentation.

Example 9

Illustrating the broader utility of this invention, the selectivity of compound 1 for AmpC was determined by measuring its activity against α-chymotrypsin (bovine pancreatic), β-trypsin (bovine pancreatic), and elastase (porcine pancreatic), all from Sigma (St. Louis, Mo.). The substrates for α-chymotrypsin (succinyl-ala-ala-pro-phe-p-nitroanilide) and β-trypsin (N-benzoyl-L-arginine ethyl ester, BAEE) were also purchased from Sigma. The elastase substrate used (elastase substrate 1, MeOSuc-Ala-Ala-Pro-Val-pNA) was purchased from Calbiochem (San Diego, Calif.). Substrates were diluted from 10 mM DMSO stock solutions, and all reactions were performed in 50 mM TRIS buffer, pH 7.0, 25° C. For α-chymotrypsin, 200 µM of substrate was used; the reactions were initiated by addition of 10 µL of a 0.1 mg/ml enzyme stock solution and monitored at 410 nm. For β-trypsin, 200 µM of BAEE was used, the reactions were initiated by the addition of 5 µL of a 0.2 mg/ml enzyme stock solution, and monitored at 260 nm. For elastase, 640 µM of elastase substrate was used, the reactions were initiated by the addition of 30 µL of a 0.2 mg/mL enzyme stock solution, and monitored at 385 nm. Initial rate fits to the absorbance data for the first 150 seconds of each reaction were used to determine reaction velocities.

Example 10

Crystal growth and structure determination. Co-crystals of AmpC/1 were grown by vapor diffusion in hanging drops equilibrated over 1.7 M potassium phosphate buffer (pH 8.7) using microseeding techniques. The initial concentration of protein in the drop was 95 µM, and the concentration of the inhibitor was 1.2 mM. The inhibitor was added to the crystallization drop in a 4% dimethylsulfoxide (DMSO), 1.7 M potassium phosphate buffer (pH 8.7) solution. Crystals appeared within 3-5 days after equilibration at 23° C.

Example 11

Data were measured on DND-CAT beam line (5IDB) of the Advanced Photon Source at Argonne National Lab at 100 K using a Mar345 image plate detector. Prior to data collection, co-crystals of AmpC/1 were immersed in a cryoprotectant solution of 20% sucrose, 1.2 mM compound 1, 1.7 M potassium phosphate, pH 8.7, for about 20 seconds, and then flash cooled in liquid nitrogen. The data set was measured from a single crystal.

Example 12

Reflections were indexed, integrated, and scaled using the HKL package (Table 3). The space group was C2, with two AmpC molecules in the asymmetric unit. Molecule 1 contained 355 residues, and molecule 2 contained 358 residues. The structure was determined by molecular replacement using a native apo AmpC structure (PDB entry 1KE4), with water molecules and ions removed, as the initial phasing model. The structure was refined using the maximum likelihood target in CNS and included simulated annealing, positional, and individual temperature factor refinement with a bulk solvent correction. Sigma A-weighted electron density maps were calculated with CNS and used in steps of manual rebuilding with the program O. The inhibitor was built into the initial observed difference density in each active site of the asymmetric unit, and the structure of the complex was further refined using CNS (Table 3). Electron density for a third inhibitor molecule was observed between the two AmpC molecules, and the inhibitor was modeled into this electron density as well.

Example 13

Antimicrobial experiments. Susceptibility testing was performed and interpreted following the guidelines of the National Committee for Clinical Laboratory Standards. To test the inhibitory activity of 1, the compound was dissolved in 50% DMSO and dilutions were performed using Luria Broth growth medium. An adequate final concentration in which to determine the minimum inhibitory concentration (MIC) was obtained where the concentration of DMSO was maintained below 5%. The MIC of the β-lactam ampicillin, in the presence and absence of 1, was determined against JM109 E. coli expressing AmpC.

TABLE 1

Kinetic characterization of DOCK predicted inhibitors of AmpC.

| Code | Structure | $K_i$ (μM) AmpC | $IC_{50}$ (μM) chymotrypsin | $IC_{50}$ (μM) trypsin | $IC_{50}$ (μM) elastase |
|---|---|---|---|---|---|
| 1 | 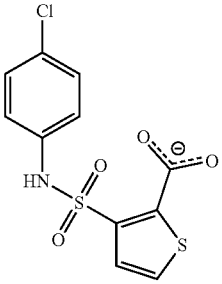 | 23 | >1,200 | >4,000 | >4,000 |
| 2 | 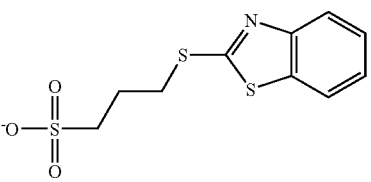 | 318 | ND[a] | ND | ND |
| 3 | 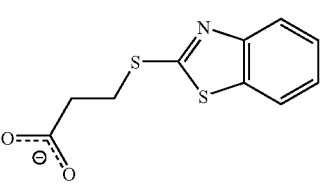 | 646 | ND | ND | ND |

[a] Not determined.

TABLE 2

Data collection and refinement statistics of AmpC/1.

| | AmpC/1 |
|---|---|
| Cell constants (Å; °) | a = 118.67 b = 76.42 c = 97.90; β = 116.63 |
| Resolution (Å) | 1.94 (1.99-1.94)[a] |
| Unique reflections | 56,580 |
| Total observations | 208,148 |
| $R_{merge}$ (%) | 5.5 (31.5) |
| Completeness (%)[b] | 97.8 (95.1) |
| $<I>/<\sigma_I>$ | 14.5 (4.2) |
| Resolution range for refinement (Å) | 20-1.94 |
| Number of protein residues | 713 |
| Number of water molecules | 352 |
| RMSD bond lengths (Å) | 0.009 |
| RMSD bond angles (°) | 1.5 |
| R-factor (%) | 17.3 |
| $R_{free}$ (%)[c] | 20.7 |
| Average B-factor, protein atoms (Å$^2$, molecule 1) | 23.8 |
| Average B-factor, protein atoms (Å$^2$, molecule 2) | 23.6 |
| Average B-factor, inhibitor atoms (Å$^2$, molecule 1) | 29.8 |
| Average B-factor, inhibitor atoms (Å$^2$, molecule 2) | 37.1 |
| Average B-factor, water molecules (Å$^2$) | 31.1 |

[a] Values in parentheses are for the highest resolution shell.
[b] Fraction of theoretically possible reflections observed.
[c] $R_{free}$ was calculated with 5% of reflections set aside randomly.

TABLE 3

Interactions in the crystallographic and DOCK-predicted complexes of AmpC with 1.

| | Distance (Å) | | |
|---|---|---|---|
| | AmpC/1 | | DOCK prediction |
| Interaction | Molecule 1 | Molecule 2 | Molecule 2 |
| S64N-O23 | 3.0 | 2.9 | 3.6 |
| S64Oγ-O23 | 2.9 | 2.8 | 3.0 |
| A318O-O23 | 2.9 | 3.0 | 2.7 |
| A318N-O23 | 2.8 | 2.9 | 2.6 |
| A318N-O24 | 3.4 | 3.4 | 3.1 |
| Wat403-O24 | 2.9 | 2.7 | 2.5 |
| Wat481-O24 | — | 2.7 | — |
| S64Oγ-O16 | 2.7 | 2.7 | 2.4 |
| K67Nζ-O16 | 3.1 | 3.1 | 4.3 |

TABLE 3-continued

Interactions in the crystallographic and DOCK-predicted complexes of AmpC with 1.

|  | Distance (Å) | | |
| --- | --- | --- | --- |
|  | AmpC/1 | | DOCK prediction |
| Interaction | Molecule 1 | Molecule 2 | Molecule 2 |
| N152Nδ2-O17 | 2.7 | 2.7 | 2.6 |
| A318O-N1 | 2.7 | 2.7 | 2.6 |

[a]Wat403 is called Wat401 in molecule 1 of the asymmetric unit.

TABLE 4

|  | MIC[a] JM109/AmpC |
| --- | --- |
| Ampicillin[b] | 512 |
| Ampicillin/1[c] | 128 |

[a]Minimum inhibitory concentration.
[b]The MIC of ampicillin in JM109 that does not express AmpC is 4 μg/ml.
[c]The ampicillin:inhibitor ratio used was 1:2.

TABLE 5

Kinetic characterization of analogs of 1.

| Code | Structure | $K_i$ (μM) AmpC |
| --- | --- | --- |
| Compound 1 | | |
| 4 | 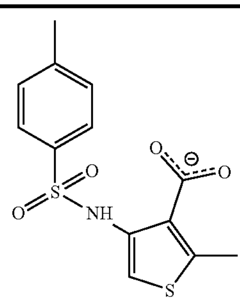 | 60 |

TABLE 5-continued

Kinetic characterization of analogs of 1.

| Code | Structure | $K_i$ (μM) AmpC |
| --- | --- | --- |
| Compound 1 | | |
| 5 | 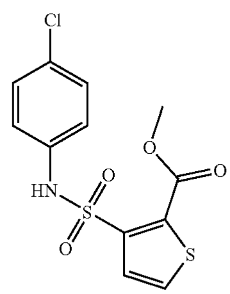 | >100 |
| 6 | 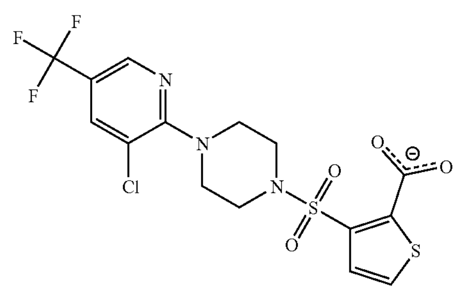 | >100 |
| 7 | 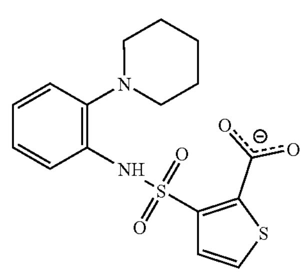 | 14 |

TABLE 5-continued
Kinetic characterization of analogs of 1.
| Code | Structure | $K_i$ (μM) AmpC |
|---|---|---|
| Compound 1 | 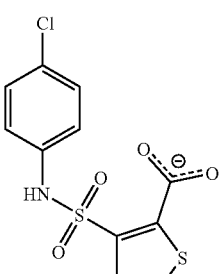 | |
| 8 | 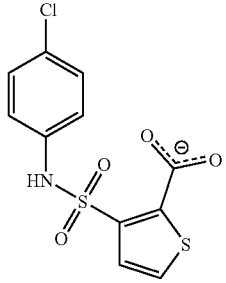 | 64 |
| Compound 1 | 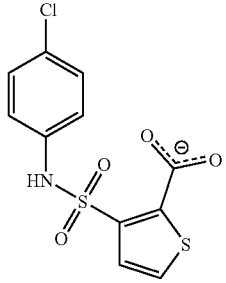 | |
| 9 | 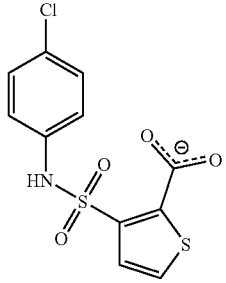 | >100 |
TABLE 6
Representative R group precursors B, are listed below.
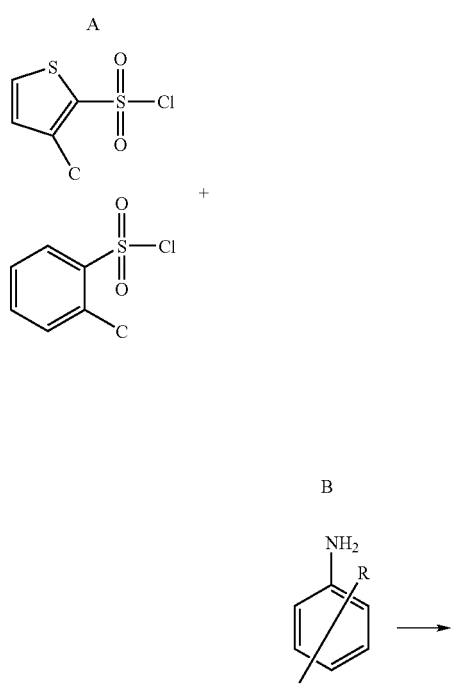

TABLE 6-continued
Representative R group precursors B, are listed below.
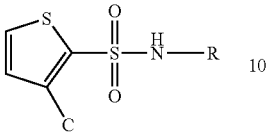 10
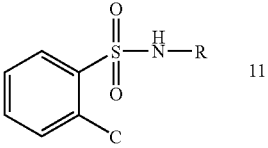 11
C = 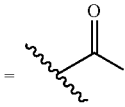
| NAME | STRUCTURE |
|---|---|
| 3-METHOXY-5-(TRIFLUOROMETHYL)ANILINE | 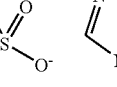 |
| 2-AMINO-3-BROMO-9-HYDROXY-FLUORENE | 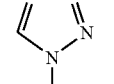 |
| 2-AMINOFLUORENE | 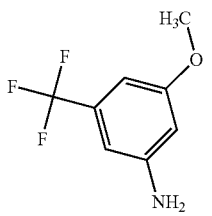 |
| ACID BLUE 25 | 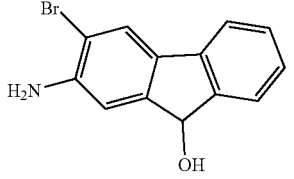 Nm⁻ |
| 4-CYCLOHEXYLANILINE | 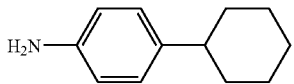 |
| 5,6,7,8-TETRAHYDRO-1-NAPHTHYLAMINE | 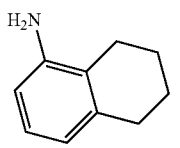 |

TABLE 6-continued
Representative R group precursors B, are listed below.
| | |
|---|---|
| 3-AMINO-4-METHOXYBENZOIC ACID | 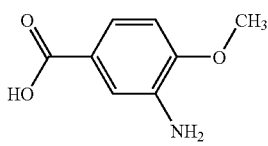 |
| SULFISOXAZOLE | 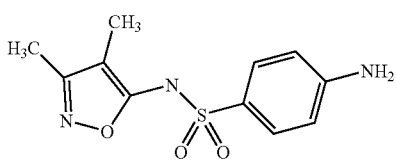 |
| 5-AMINOINDAN | 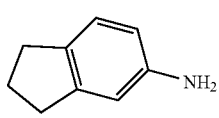 |
| J ACID | 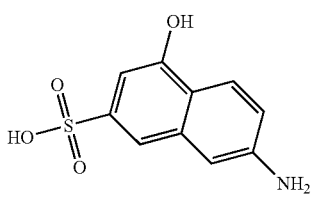 |
| 1-NAPHTHYLAMINE | 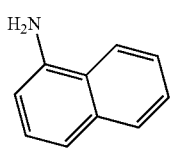 |
| 4-AMINO-1-NAPHTHALENECARBONITRILE | 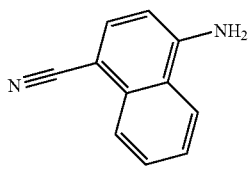 |
| 4-PHENYLAZO-1-NAPHTHYLAMINE | 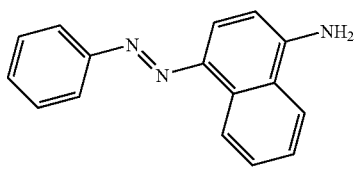 |
| 3-AMINO-2-NAPHTHOL | 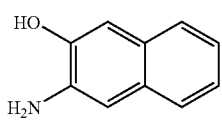 |
| 2,3-DIAMINONAPHTHALENE | 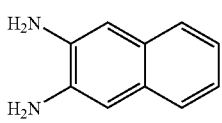 |
| SULFAMOXOL | 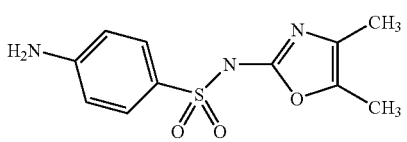 |

TABLE 6-continued
Representative R group precursors B, are listed below.
| | |
|---|---|
| 1-(2-AMINOPHENYL)PYRROLE | 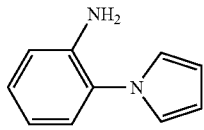 |
| 2-AMINO-6,8-DIHYDROXYPURINE | 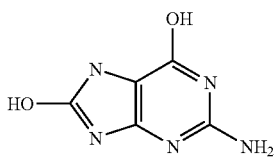 |
| 2-AMINOPURINE | 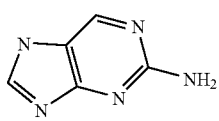 |
| 5-AMINOINDOLE | 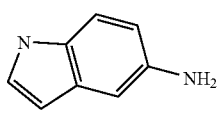 |
| 4-AMINOPYRAZOLO[3,4-D]PYRIMIDINE | 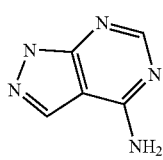 |
| 4-AMINO-6-HYDROXYPYRAZOLO(3,4-D)PYRIMIDINE | 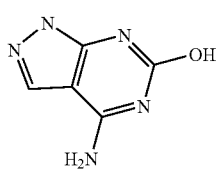 |
| N1-(6-INDAZOLYL)SULFANILAMIDE | 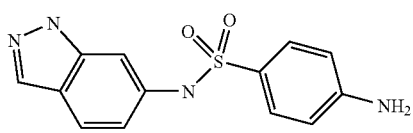 |
| 8-AZAADENINE | 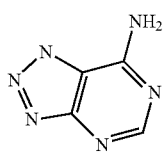 |
| 8-BROMOADENOSINE | 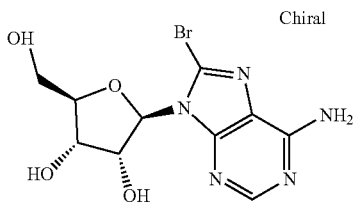 |
| 2-(4-AMINOPHENYL)-6-METHYLBENZOTHIAZOLE | 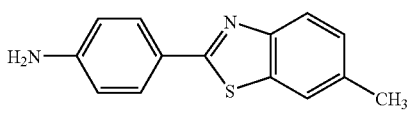 |

TABLE 6-continued
Representative R group precursors B, are listed below.
3,4-METHYLENEDIOXYANILINE 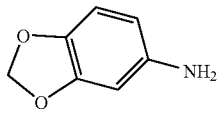
N-(4-AMINO-2-METHYLPHENYL)-4-CHLOROPHTHALIMIDE 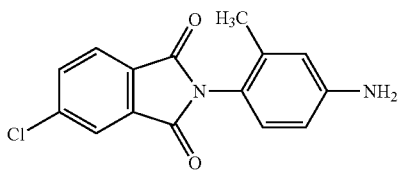
ATRAZINE-DESETHYL DESISOPROPYL 
MELAMINE 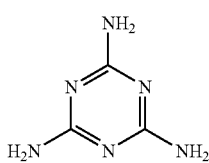
SULFADIAZINE 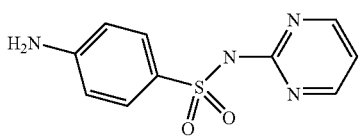
SULFAMETHAZINE 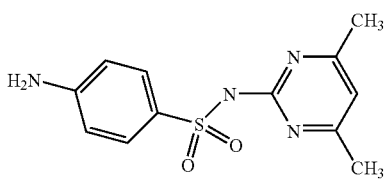
6-AMINO-5-NITROSO-2-THIOURACIL 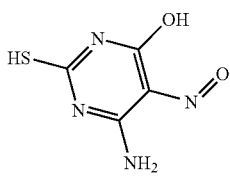
2-AMINOPYRIMIDINE 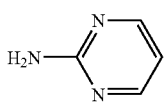
2-AMINO-5-NITROPYRIMIDINE 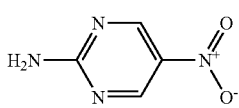
AMINOPYRAZINE 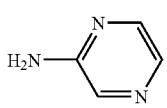

TABLE 6-continued
Representative R group precursors B, are listed below.
4-[N-(2-AMINO-3-CYANO-5-PYRA-ZINYLMETHYL)-AMINO]BENZOIC ACID
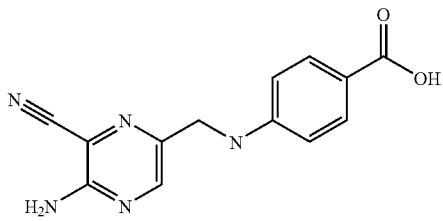
5-ACETOXYMETHYL-2-AMINO-3-CYANOPYRAZINE
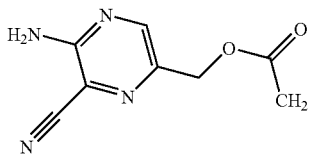
3-AMINOPYRAZINE-2-CARBOXYLIC ACID
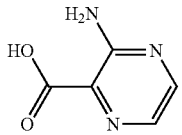
4-MORPHOLINOANILINE
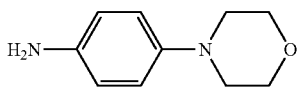
2-AMINOPYRIDINE
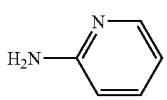
2-AMINO-3-BENZYLOXYPYRIDINE
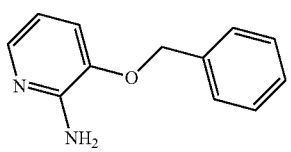
6-AMINONICOTINIC ACID
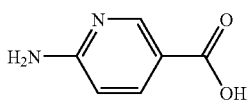
6-AMINONICOTINAMIDE
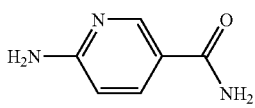
3-AMINO-1,2,4-TRIAZINE
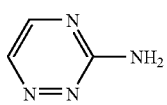
2-AMINO-6,7-DIMETHYL-4-HYDROXYPTERIDINE
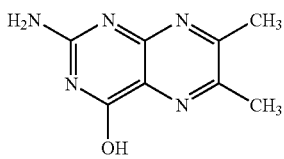

TABLE 6-continued
Representative R group precursors B, are listed below.
2,4-DIAMINO-6-(HYDROXYMETHYL)PTERIDINE
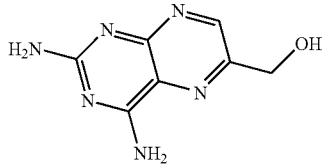
5,7-DIMETHYL[1,8]NAPHTHYRIDIN-2-AMINE
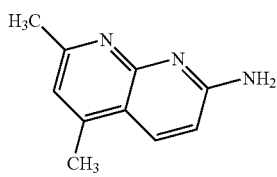
4-AMINO-2-METHYLQUINOLINE
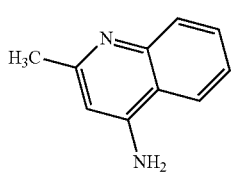
3,4-ETHYLENEDIOXYANILINE
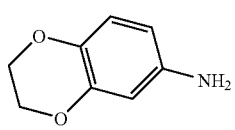
LUMINOL
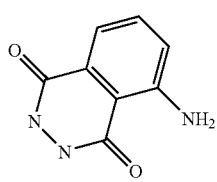
4-NITROANTHRANILIC ACID
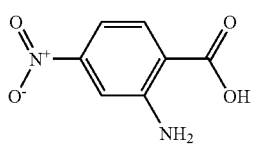
4-AMINOBENZHYDRAZIDE
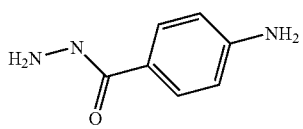
ANILINE
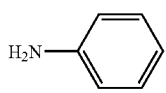
2-(3-AMINO-4-CHLOROBENZOYL)BENZOIC ACID
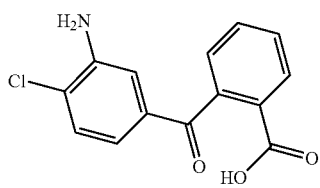
N-PHENYL-O-PHENYLENEDIAMINE
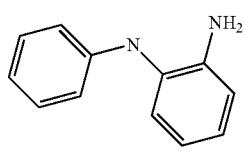

TABLE 6-continued
Representative R group precursors B, are listed below.
| | |
|---|---|
| 2-AMINOPHENOL-4-SULFONIC ACID | 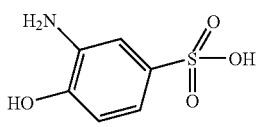 |
| 2-AMINOBIPHENYL | 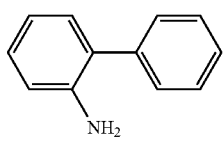 |
| 2-AMINO DIPHENYL SULFONE | 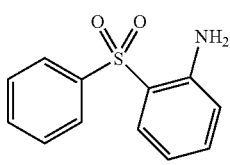 |
| O-AMINOBENZALDEHYDE | 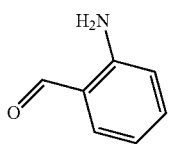 |
| FAST RED VIOLET LB BASE | 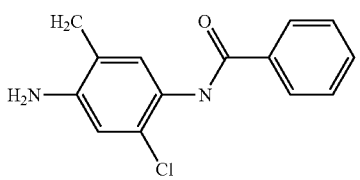 |
| PHENYL 4-AMINOSALICYLATE | 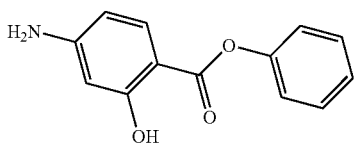 |
| 4-AMINOSALICYLIC ACID | 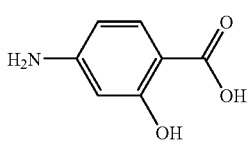 |
| 5-PHENYL-O-ANISIDINE | 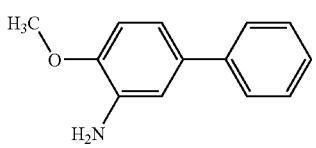 |
| 3-3'-DIAMINODIPHENYL SULFONE | 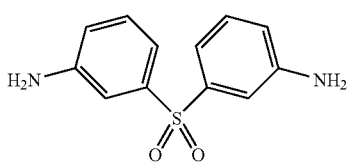 |
| 4-AMINODIPHENYLAMINE | 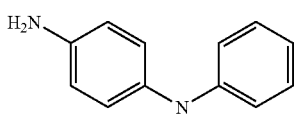 |

TABLE 6-continued

Representative R group precursors B, are listed below.

P-AMINOOXANILIC ACID
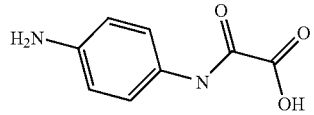

4-AMINOAZOBENZENE
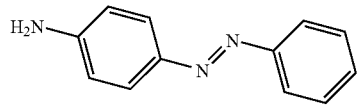

4-AMINOPHENOL

2-AMINO-5-HYDROXYBENZOIC ACID
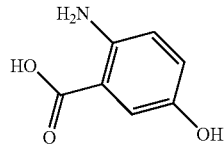

4-AMINO-DI-BENZENE-SULFONAMIDE
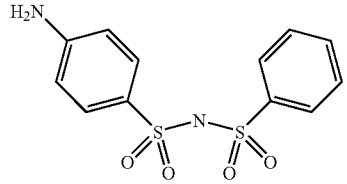

SULFANILIC ACID
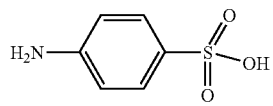

4-AMINOHIPPURIC ACID
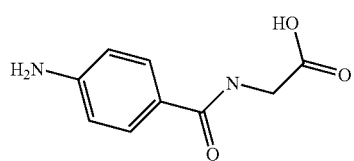

4-AMINOBENZOIC ACID
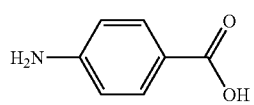

We claim:

1. A pharmaceutical composition comprising a pharmaceutically-acceptable carrier and a compound having a formula

A-SO$_2$—NH—R wherein A is a thiophen-3-yl moiety substituted with a carboxylate group and a pharmaceutically-acceptable cation; at the 2-position of said thiophenyl moiety and adjacent said SO$_2$ moiety; and wherein R is a phenyl moiety with a 4-chloro substituent.

2. The composition of claim 1 further comprising a β-lactam antibiotic.

* * * * *